(12) United States Patent
Tatara et al.

(10) Patent No.: US 11,497,397 B2
(45) Date of Patent: Nov. 15, 2022

(54) OPHTHALMOLOGIC APPARATUS

(71) Applicant: TOPCON CORPORATION, Tokyo (JP)

(72) Inventors: Yoko Tatara, Kita-ku (JP); Michiko Nakanishi, Katsushika-ku (JP); Shunichi Morishima, Kawagoe (JP)

(73) Assignee: TOPCON CORPORATION, Tokyo (JP)

( * ) Notice: Subject to any disclaimer, the term of this patent is extended or adjusted under 35 U.S.C. 154(b) by 893 days.

(21) Appl. No.: 16/289,679

(22) Filed: Mar. 1, 2019

(65) Prior Publication Data

US 2019/0298168 A1   Oct. 3, 2019

(30) Foreign Application Priority Data

Mar. 27, 2018   (JP) .............................. JP2018-059894

(51) Int. Cl.
*A61B 3/103* (2006.01)
*A61B 3/00* (2006.01)
(Continued)

(52) U.S. Cl.
CPC ............ *A61B 3/103* (2013.01); *A61B 3/0025* (2013.01); *A61B 3/102* (2013.01); *A61B 3/107* (2013.01);
(Continued)

(58) Field of Classification Search
CPC ....... A61B 3/103; A61B 3/0025; A61B 3/102; A61B 3/1035; A61B 3/107; A61B 3/12; A61B 3/14
(Continued)

(56) References Cited

U.S. PATENT DOCUMENTS

2012/0063665 A1   3/2012 Wang et al.
2012/0307014 A1   12/2012 Wang
(Continued)

FOREIGN PATENT DOCUMENTS

JP   62224330 A  *  2/1987
JP   S62-224330 A   10/1987
(Continued)

OTHER PUBLICATIONS

Extended European Search Report dated Aug. 22, 2019, issued in corresponding European Patent Application No. 19160240.8, 8 pages.
(Continued)

*Primary Examiner* — Mohammed A Hasan
(74) *Attorney, Agent, or Firm* — Xsensus LLP

(57) ABSTRACT

An ophthalmologic apparatus includes an objective lens, a refractive power measurement optical system, an inspection optical system, and a corneal shape measurement optical system. The refractive power measurement optical system projects light onto a subject's eye via the objective lens and detects returning light from the subject's eye. The inspection optical system includes an optical scanner. The inspection optical system deflects light from a light source, projects the light deflected by the optical scanner onto the subject's eye via the objective lens, and detects returning light from the subject's eye. The corneal shape measurement optical system projects an arc-like or circumferential measurement pattern from an outer edge side of the objective lens onto the subject's eye and detects returning light from a cornea of the subject's eye. When a working distance is WD, a distance from a corneal apex of the subject's eye to a pupil of the subject's eye is d1, a distance from the pupil to a fundus of the subject's eye is d2, and a scan range by the optical scanner is SA square, a diameter of the objective lens is greater than or equal to ((WD+d1)×SA/d2).

5 Claims, 7 Drawing Sheets

(51) Int. Cl.
　　　*A61B 3/10*　　　(2006.01)
　　　*A61B 3/12*　　　(2006.01)
　　　*A61B 3/14*　　　(2006.01)
　　　*A61B 3/107*　　(2006.01)

(52) U.S. Cl.
　　　CPC .............. *A61B 3/1035* (2013.01); *A61B 3/12* (2013.01); *A61B 3/14* (2013.01)

(58) Field of Classification Search
　　　USPC ........................................................ 351/205
　　　See application file for complete search history.

(56) References Cited

U.S. PATENT DOCUMENTS

| | | |
|---|---|---|
| 2013/0077046 A1 | 3/2013 | Kim et al. |
| 2014/0288419 A1 | 9/2014 | Wang et al. |
| 2015/0211838 A1 | 7/2015 | Wang |
| 2019/0008378 A1 | 1/2019 | Hayashi et al. |

FOREIGN PATENT DOCUMENTS

| | | | | |
|---|---|---|---|---|
| JP | 11347002 A | * | 12/1999 | |
| JP | H11-347002 A | | 12/1999 | |
| JP | 2006-055464 A | | 3/2006 | |
| JP | 2013-518695 A | | 5/2013 | |
| JP | 2013518695 A | * | 5/2013 | |
| JP | 2015-033650 A | | 2/2015 | |
| JP | 2015033650 A | * | 2/2015 | ............. A61B 3/102 |
| JP | 2017-136215 A | | 8/2017 | |
| JP | 2017-136217 A | | 8/2017 | |
| JP | 2017136215 A | * | 8/2017 | ........... A61B 3/0025 |
| WO | 2011063220 A2 | | 5/2011 | |
| WO | 2017135015 A1 | | 8/2017 | |

OTHER PUBLICATIONS

Office Action dated Jan. 25, 2022, in corresponding Japanese patent Application No. 2018-059894, 12 pages.

Japanese Office Action dated Aug. 2, 2022, in corresponding Japanese Application No. 2018-059894, 25 pp.

* cited by examiner

| | | AVERAGE DIAMETER | INNER DIAMETER | OUTER DIAMETER |
|---|---|---|---|---|
| MEASUREMENT RANGE RADIUS | h [mm] | 1.5 | 1.475 | 1.525 |
| CORNEAL CURVATURE RADIUS | R [mm] | 8 | 8 | 8 |
| PROJECTION ANGLE | α [deg] | 21.61385 | 21.24939 | 21.97852 |
| DISTANCE BETWEEN KERATO PLATE AND CORNEAL APEX | L [mm] | 49.5 | 49.5 | 49.5 |
| DIAMETER OF KERATO PATTERN | 2H [mm] | 42.22455 | 41.44778 | 43.00543 |

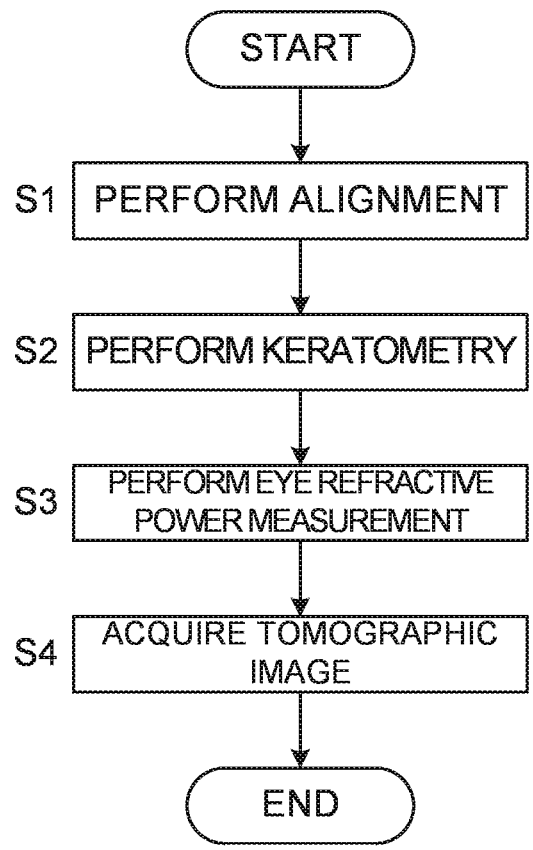

OPHTHALMOLOGIC APPARATUS

CROSS-REFERENCE TO RELATED APPLICATION

This application is based upon and claims the benefit of priority from Japanese Patent Application No. 2018-059894, filed Mar. 27, 2018; the entire contents of which are incorporated herein by reference.

FIELD

Embodiments according to present invention described herein relate to an ophthalmologic apparatus.

BACKGROUND

Ophthalmologic apparatuses capable of performing a plurality of inspections and measurements for a subject's eye are known. The inspections and the measurements for the subject's eye include a subjective inspection and an objective measurement. The subjective inspection is to acquire the result based on the responses from the subject. The objective measurement is to acquire information on the subject's eye mainly by the use of a physical method without referring to the responses from the subject.

For example, Japanese Unexamined Patent Application Publication No. 2017-136215 discloses an ophthalmologic apparatus capable of performing the subjective inspection and the objective measurement. In this ophthalmologic apparatus, a refractive power measurement of the subject's eye, a keratometry of the subject's eye, photographing using optical coherence tomography, and a measurement using optical coherence tomography can be performed.

SUMMARY

One aspect of some embodiments is an ophthalmologic apparatus including: an objective lens; a refractive power measurement optical system configured to project light onto a subject's eye via the objective lens and to detect returning light from the subject's eye; an inspection optical system that includes an optical scanner and is configured to deflect light from a light source, to project the light deflected by the optical scanner onto the subject's eye via the objective lens, and to detect returning light from the subject's eye; and a corneal shape measurement optical system configured to project an arc-like or circumferential measurement pattern from an outer edge side of the objective lens onto the subject's eye and to detect returning light from a cornea of the subject's eye, wherein when a working distance is WD, a distance from a corneal apex of the subject's eye to a pupil of the subject's eye is d1, a distance from the pupil to a fundus of the subject's eye is d2, and a scan range by the optical scanner is SA square, a diameter of the objective lens is greater than or equal to $((WD+d1) \times SA/d2)$.

Another aspect of some embodiments is an ophthalmologic apparatus including: an objective lens; a refractive power measurement optical system configured to project light onto a subject's eye via the objective lens and to detect returning light from the subject's eye; an inspection optical system that includes an optical scanner and is configured to deflect light from a light source, to project the light deflected by the optical scanner onto the subject's eye via the objective lens, and to detect returning light from the subject's eye; and a corneal shape measurement optical system configured to project an arc-like or circumferential measurement pattern from an outer edge side of the objective lens onto the subject's eye and to detect returning light from a cornea of the subject's eye, wherein the corneal shape measurement optical system includes: a keratometry light source; and a keratometry plate that is disposed between the keratometry light source and the subject's eye and is formed a light transmitting part which penetrates light from the keratometry light source, wherein the corneal shape measurement optical system is configured to project the measurement pattern onto the cornea of the subject's eye around an optical axis of the objective lens, and when a distance between the corneal apex of the subject's eye and the keratometry plate is L, a height of an image based on the measurement pattern with respect to an optical axis of the objective lens is h, a radial width of the measurement pattern is $\Delta t$, and a corneal curvature radius of the subject's eye is R, the diameter of the objective lens is less than $2 \times ((L+(R-\sqrt{(R^2-h^2)})) \times \tan(2 \times \sin^{-1}(h/R)) + h - \Delta t/2)$.

BRIEF DESCRIPTION OF THE DRAWINGS

FIG. 8 is a schematic diagram illustrating a flow of the operation example of the ophthalmologic apparatus according to the embodiments.

DETAILED DESCRIPTION

Figure 1:
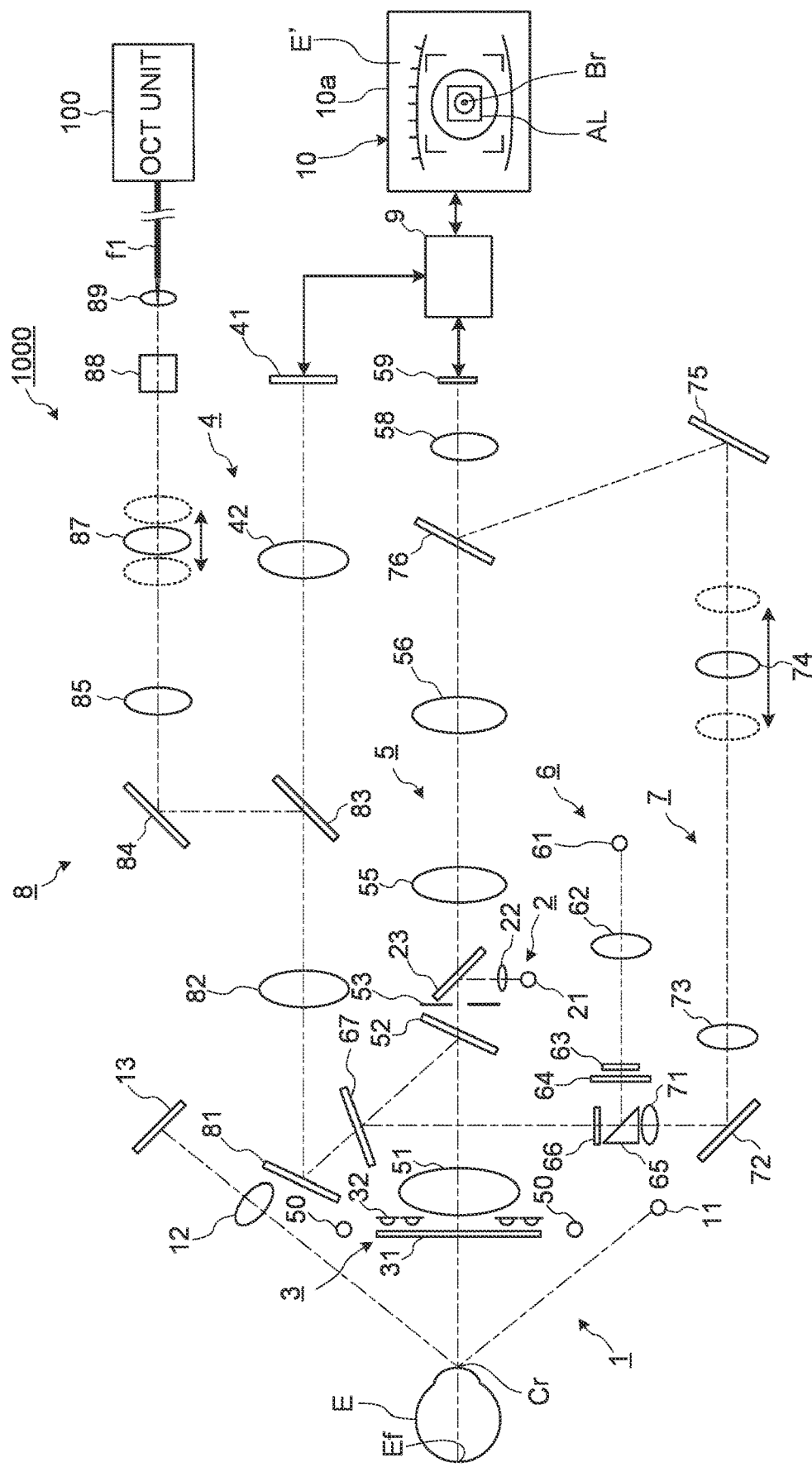
FIG. 1 is a schematic diagram illustrating an example of a configuration of an optical system of an ophthalmologic apparatus according to embodiments.

In ophthalmologic apparatuses capable of performing a plurality of inspections and measurements, by sharing the objective lens with a plurality of optical systems corresponds to the type of objective measurement, the apparatus can be reduced the size and the cost.

However, there is an optimum working distance for each of the plurality of optical systems. Therefore, when the working distance of the ophthalmologic apparatus is set to an optimum distance for one of the plurality of optical systems, the measurement range using another optical system becomes narrower or the accuracy of measurement decreases.

For example, when the working distance of the ophthalmologic apparatus is set to an optimum distance for a refractive power measurement optical system, the scan range by an OCT optical system for performing optical coherence tomography (OCT) becomes narrower. On the other hand, when the working distance of the ophthalmologic apparatus is set to an optimum distance for the OCT optical system, the measurement results of the refractive power measurement optical system becomes susceptible to instrument myopia. Thereby, it is necessary to increase a diameter of the objective lens. However, if the diameter of the objective lens is increased, it becomes difficult to project a measurement pattern used for a keratometry. Thereby a corneal shape can not be measured with high accuracy.

According to some embodiments of the present invention, a new technique for optimizing the diameter of the objective lens without deteriorating the measurement range and the measurement accuracy by a plurality of optical systems corresponding to the type of the objective measurement can be provided.

Referring now to the drawings, exemplary embodiments of an ophthalmologic apparatus according to the present invention are described below. Any of the contents of the documents cited in the present specification and arbitrary known techniques may be applied to the embodiments below.

The ophthalmologic apparatus according to embodiments is capable of performing a refractive power measurement (refractometry), a keratometry, and a scan measurement. In the scan measurement, measurement results are obtained by deflecting light for measurement, projecting the deflected light onto the subject's eye, and detecting returning light from the subject's eye. Examples of scan measurements include measurements or photographing using optical coherence tomography, measurements or photographing using an SLO optical system, and the like. A case where the ophthalmologic apparatus according to the embodiments perform OCT on an anterior segment or a fundus as the scan measurement will be described.

Hereinafter, the case of using the method of swept source type OCT will be described in detail in the embodiments. However, the configuration according to the embodiments can be applied to ophthalmologic apparatus using another type OCT (for example, the spectral domain type or the time domain type).

An ophthalmologic apparatus according to some embodiments further includes a subjective inspection optical system for perform subjective inspection and an objective measurement system for performing other objective measurement.

The subjective inspection is a method for measurement to acquire information using the responses from the subject. Examples of the subjective inspection include a visual field test, and subjective refractometry such as a far vision test, a near vision test, a contrast test, a glare test and the like.

The objective measurement is a method for measurement to acquire information on the subject's eye mainly by the use of a physical method without referring to the responses from the subject. The objective measurements include a measurement for acquiring the characteristics of the subject's eye and photographing for acquiring an image of the subject's eye. Examples of the other objective measurements include a tonometry, a fundus photography, and the like.

Hereinafter, a fundus conjugate position is a position substantially optically conjugate with a fundus of a subject's eye in a state where alignment is completed, and means a position optically conjugate with the fundus of the subject's eye or the vicinity of the position. Similarly, a pupil conjugate position is a position substantially optically conjugate with a pupil of a subject's eye in a state where alignment is completed, and means a position optically conjugate with the pupil of the subject's eye or the vicinity of the position.

<Configuration of Optical System>

FIG. 1 illustrates an example of the configuration of an optical system of the ophthalmologic apparatus according to the embodiments. The ophthalmologic apparatus 1000 according to the embodiments includes an optical system for observing the subject's eye E, an optical system for inspecting the subject's eye E, and a dichroic mirror that wavelength-separates the optical paths of these optical systems. An anterior segment observation (imaging) system 5 is provided as the optical system for observing the subject's eye E. An OCT optical system, a refractometry optical system (refractive power measurement optical system), and the like are provided as the optical system for inspecting the subject's eye E.

The ophthalmologic apparatus 1000 includes a Z alignment system 1, a XY alignment system 2, a keratometry system 3, a fixation projection system 4, the anterior segment observation system 5, a refractometry projection system 6, a refractometry light reception system 7, and an OCT optical system 8. Hereinafter, for example, it is assumed that light with 940 nm to 1000 nm is used in the anterior segment observation system 5, light with 830 nm to 880 nm is used in the refractometry optical system (refractometry projection system 6, refractometry light reception system 7), light with 400 nm to 700 nm is used in the fixation projection system 4, and light with 1000 nm to 1100 nm is used in the OCT optical system 8.

(Anterior Segment Observation System 5)

The anterior segment observation system 5 is configured to acquire a moving image of an anterior segment of the subject's eye E. In an optical system passing through the anterior segment observation system 5, an imaging plane of an imaging element 59 is arranged at the pupil conjugate position. An anterior segment illumination light source 50 irradiates illumination light (for example, infrared light) on the anterior segment of the subject's eye E. The light reflected from the anterior segment of the subject's eye E passes through an objective lens 51, penetrates a dichroic mirror 52, passes through the aperture part formed in a diaphragm (telecentric diaphragm) 53, penetrates a half mirror 23, passes through relay lenses 55 and 56, and penetrates a dichroic mirror 76. The dichroic mirror 52 combines (or separates) the optical path of the refractometry optical system with the optical path of the anterior segment optical system 5. The dichroic mirror 52 is disposed so that its optical path combining surface for combining these optical paths is inclined with respect to the optical axis of the objective lens 51. The light penetrating the dichroic mirror 76 forms an image on the imaging surface of the imaging element 59 (area sensor) by an imaging lens 58. The imaging element 59 performs an imaging and a signal outputting at a predetermined rate. The output (video signal) of the imaging element 59 is input to a processing unit (processor) 9 described after. The processing unit 9 displays an anterior segment image E' based on this video signal on a display screen 10a of a display unit 10. The anterior segment image E' is an infrared moving image for example.

(Z Alignment System 1)

The Z alignment system 1 is configured to project light (infrared light) for performing alignment in an optical axis direction (front-back directions, Z direction) of the anterior segment observation system 5 onto the subject's eye E. Light emitted from a Z alignment light source 11 is projected onto a cornea Cr of the subject's eye E, is reflected by the cornea Cr, and forms an image on a line sensor 13 by an imaging lens 12. When the position of a corneal apex changes in the optical axis direction of the anterior segment observation system 5, the projection position of the light onto the line sensor 13 changes. The processing unit 9 obtains a position of the corneal apex of the subject's eye E based on the projection position of the light onto the line sensor 13 and controls a mechanism for moving the optical system to perform Z alignment based on this.

(XY Alignment System 2)

The XY alignment system 2 is configured to project light (infrared light) for performing alignment in a direction (left-right directions (X direction), up-down directions (Y direction)) orthogonal to the optical axis direction of the anterior segment observation system 5 onto the subject's eye E. The XY alignment system 2 includes a XY alignment light source 21 and a collimator lens 22 that are provided in an optical path branched from the optical path of the anterior segment observation system 5 by the half mirror 23. The light emitted from the XY alignment light source 21 passes through the collimator lens 22, is reflected by the half mirror 23, and is projected onto the subject's eye E through the anterior segment observation system 5. Reflected light from the cornea Cr of the subject's eye E is guided to the imaging element 59 through the anterior segment observation system 5.

An image (bright spot image) Br based on the reflected light is included in the anterior segment image E'. The processing unit 9 controls the display unit to display an alignment mark AL and the anterior segment image E' including the bright spot image Br on the display screen of the display unit. In the case of performing XY alignment manually, a user can perform an operation for moving the optical system so as to guide the bright spot image Br in the alignment mark AL. In the case of performing XY alignment automatically, the processing unit 9 controls a mechanism for moving the optical system so as to cancel a displacement of the bright spot image Br with respect to the alignment mark AL.

(Keratometry System 3)

The keratometry system 3 is configured to project a ring-shaped light flux (infrared light) for measuring a shape of the cornea Cr of the subject's eye E onto the cornea Cr. A kerato plate (keratometry plate) 31 is disposed between the objective lens 51 and the subject's eye E. A kerato-ring light source (keratometry ring light source, keratometry light source) 32 is provided on the back side (the objective lens 51 side) of the kerato plate 31. In the kerato plate 31, a kerato (keratometry) pattern (transmitting part, light transmitting part) that penetrates light form the kerato-ring light source 32 is formed along a circumference around the optical axis of the objective lens 51. It should be noted that the keratometry pattern may be formed in an arc shape (a part of the circumference) around the optical axis of the objective lens 51. By illuminating the kerato plate 31 with light from the kerato-ring light source 32, the ring-shaped light flux (arc-like or circumferential (circular) measurement pattern) is projected onto the cornea Cr. The reflected light (kerato-ring image) from the cornea Cr of the subject's eye E is detected by the imaging element 59 along with the anterior segment image E'. The processing unit 9 calculates a corneal shape parameter representing a shape of the cornea Cr, by performing a known calculation based on this kerato-ring image.

(Refractometry Projection System 6 and Refractometry Light Reception System 7)

The refractometry optical system includes the refractometry projection system 6 and the refractometry light reception system 7 which are used for refractive power measurement. The refractometry projection system 6 is configured to project light flux (a ring-shaped light flux, for example) (infrared light) for measuring refractive power onto the fundus Ef. The refractometry light reception system 7 is configured to receive returning light of the light flux from the subject's eye E. The refractometry projection system 6 is provided in an optical path branched by the perforated prism 65 provided in an optical path of the refractometry light reception system 7. A hole part formed in the perforated prism 65 is arranged at the pupil conjugate position. In an optical system passing through the refractometry light reception system 7, the imaging surface of the imaging element 59 is arranged at the fundus conjugate position.

In some embodiments, the refractometry light source 61 is a SLD (Super Luminescent Diode) light source which is a high-intensity light source. The refractometry light source 61 is movable in an optical axis direction. The refractometry light source 61 is arranged at the fundus conjugate position. The light emitted from the refractometry light source 61 passes through the relay lens 62 and is incident on a conical surface of the conical prism 63. The light incident on the conical surface is deflected and emits from a bottom surface of the conical prism 63. The light emitted from the bottom surface of the conical prism 63 passes through a ring-shaped light transmission part formed in a ring diaphragm 64. The light (ring-shaped light flux) passing through the light transmission part of the ring diaphragm 64 is reflected on a reflective surface formed around the hole part of the perforated prism 65, passes through a rotary prism 66, and is reflected by the dichroic mirror 67. The light reflected by the dichroic mirror 67 is reflected by the dichroic mirror 52, passes through the objective lens 51, and is projected onto the fundus Ef. The rotary prism 66 is used for averaging the light quantity distribution of the ring-shaped light flux with respect to the blood vessel or the diseased site of the fundus Ef or for reducing the speckle noise caused by the light source.

Returning light of the ring-shaped light flux projected onto the fundus Ef passes through the objective lens 51, and is reflected by the dichroic mirrors 52 and 67. The returning light reflected by the dichroic mirror 67 passes through the rotary prism 66, passes through the hole part of the perforated prism 65, passes through a relay lens 71, is reflected by a reflective mirror 72, and passes through a relay lens 73 and a focusing lens 74. The focusing lens 74 is movable along an optical axis of the refractometry light reception system 7. The light passing through the focusing lens 74 is reflected by the reflective mirror 75, is reflected by a dichroic mirror 76, and forms an image on the imaging surface of the imaging element 59 by the imaging lens 58. The processing unit 9 calculates a refractive power value of the subject's eye E by performing the known calculation based on the output of the imaging element 59. For example, refractive power value includes a spherical power, a degree of astigmatism, and an astigmatic axis angle, or an equivalent spherical power.

(Fixation Projection System 4)

The OCT optical system 8, which will be described after, is provided in the optical path wavelength-separated from the optical path of the refractometry optical system by the dichroic mirror 67. The fixation projection system 4 is provided in the optical path wavelength-separated from the optical path of the OCT optical system 8 by the dichroic mirror 83.

The fixation projection system 4 is configured to present a fixation target to the subject's eye E. Under the control of the processing unit 9, a liquid crystal panel 41 displays a pattern representing the fixation target. By changing the display position of the fixation target on the screen of the liquid crystal panel 41, the fixation position of the subject's eye E can be changed. Examples of the fixation position of the subject's eye E include a position for acquiring an image centered at a macular region of the fundus Ef, a position for acquiring an image centered at an optic disc, and a position for acquiring an image centered at the fundus center between the macular region and the optic disc. The display position of the pattern representing the fixation target can be arbitrarily changed.

Light from the liquid crystal panel 41 passes through a relay lens 42, penetrates a dichroic mirror 83, passes through a relay lens 82, is reflected by a reflective mirror 81, penetrates a dichroic mirror 67, and is reflected by the dichroic mirror 52. The light reflected by the dichroic mirror 52 passes through the objective lens 51 and is projected onto a fundus Ef. The liquid crystal panel 41 (or the liquid crystal panel 41 and the relay lens 42) is movable in the optical axis direction.

(OCT Optical System 8)

The OCT optical system 8 is an optical system for performing OCT measurement. The position of the focusing lens 87 is adjusted so that an end face of an optical fiber f1 and a photographing site (fundus Ef or the anterior segment) are optically conjugate with each other based on the result of the refractometry performed before the OCT measurement.

The OCT optical system 8 is provided in the optical path wavelength-separated from the optical path of the refractometry optical system by the dichroic mirror 67. The optical path of the above fixation projection system 4 is coupled with the optical path of the OCT optical system 8 by the dichroic mirror 83. Thereby, the optical axes of the OCT optical system 8 and the fixation projection system 4 can be coupled coaxially.

Figure 2:
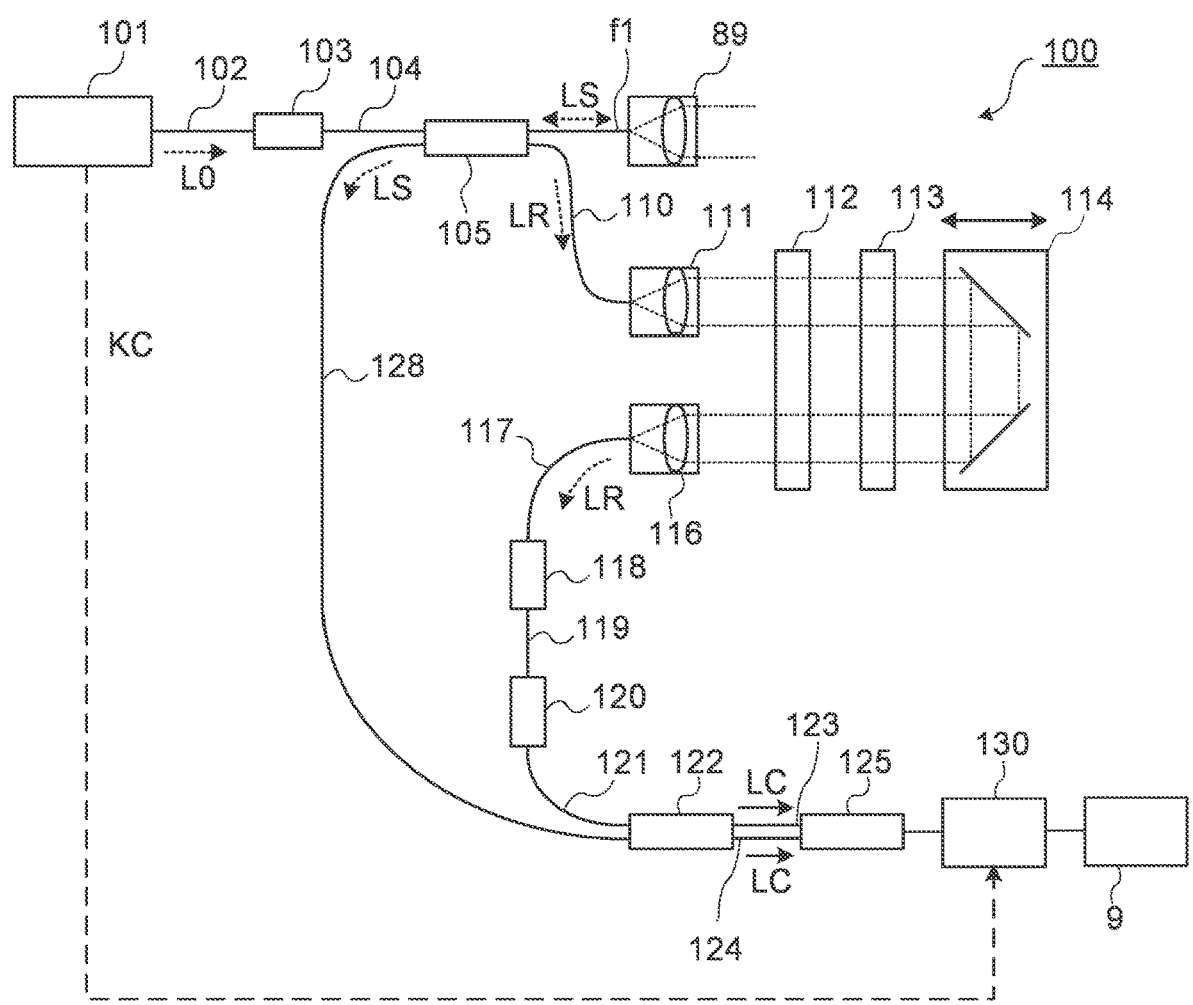
FIG. 2 is a schematic diagram illustrating an example of a configuration of an optical system of the ophthalmologic apparatus according to the embodiments.

The OCT optical system 8 includes an OCT unit 100. As illustrated in FIG. 2, in the OCT unit 100, like general swept-source-type OCT apparatuses, an OCT light source 101 includes a wavelength tunable type (a wavelength scanning type) light source capable of sweeping (scanning) the wavelengths of emitted light. The wavelength tunable type light source includes a laser light source that includes a resonator. The OCT light source 101 temporally changes the output wavelength in the near infrared wavelength band which cannot be visually recognized by the human eye.

As illustrated by an example in FIG. 2, the OCT unit 100 is provided with an optical system for performing swept source OCT. This optical system includes an interference optical system. This interference optical system has a function that splits light from the wavelength tunable type (wavelength scanning type) light source into measurement light and reference light, a function that makes the returning light of the measurement light from the subject's eye E and the reference light having traveled through a reference optical path interfere with each other and generates interference light, and a function that detects the interference light. The detection result (detection signal, interference signal) of the interference light obtained by the interference optical system is a signal indicating a spectrum of the interference light, and is sent to the processing unit 9.

The OCT light source 101 includes a near-infrared tunable laser which changes the wavelength of the emitted light (a wavelength range of 1000 nm to 1100 nm) at high speed, for example. The light L0 output from the OCT light source 101 is guided to the polarization controller 103 through the optical fiber 102, and the polarization state of the light L0 is adjusted. The light L0 whose polarization state has been adjusted is guided to the fiber coupler 105 through the optical fiber 104. The fiber coupler 105 splits the light L0 into the measurement light LS and the reference light LR.

The reference light LR is guided to the collimator 111 through the optical fiber 110. The reference light LR is converted into a parallel light beam by the collimator 111. Then, the reference light LR is guided to the corner cube 114 via the optical path length correction member 112 and the dispersion compensation member 113. The optical path length correction member 112 acts so as to match the optical path length of the reference light LR with the optical path length of the measurement light LS. The dispersion compensation member 113 acts so as to match the dispersion characteristics between the reference light LR and the measurement light LS. The corner cube 114 is movable in the incident direction of the reference light LR. With this, the length of the optical path of the reference light LR is changed.

The reference light LR that has traveled through the corner cube 114 passes through the dispersion compensation member 113 and the optical path length correction member 112, is converted from the parallel light beam to the convergent light beam by a collimator 116, and enters an optical fiber 117. The reference light LR that has entered the optical fiber 117 is guided to a polarization controller 118, and the polarization state of the reference light LR is adjusted. Then the reference light LR is guided to an attenuator 120 through an optical fiber 119, and the light amount of the reference light LR is adjusted. After that, the reference light LR is guided to a fiber coupler 122 through an optical fiber 121.

Meanwhile, the measurement light LS generated by the fiber coupler 105 is guided through the optical fiber f1, is made into the parallel light beam by the collimator lens unit 89, is reflected by the dichroic mirror 83 via an optical scanner 88, the focusing lens 87, relay lens 85, and the reflective mirror 84.

The optical scanner 88 deflects the measurement light LS in a one-dimensionally or two-dimensional manner. The optical scanner 88 includes a first galvano mirror and a second galvano mirror, for example. The first galvano mirror deflects the measurement light LS so as to scan the photographing site (fundus Ef or the anterior segment) in a horizontal direction orthogonal to the optical axis of the OCT optical system 8. The second galvano mirror deflects the measurement light LS deflected by the first galvano mirror so as to scan the photographing site in a vertical direction orthogonal to the optical axis of the OCT optical system 8. Examples of scan modes with the measurement light LS performed by the optical scanner 88 like this include horizontal scan, vertical scan, cross scan, radial scan, circle scan, concentric scan, helical (spiral) scan, and the like.

The measurement light LS reflected by the dichroic mirror 83 passes through the relay lens 82, is reflected by the reflective mirror 81, penetrates the dichroic mirror 67, is reflected by the dichroic mirror 52, is refracted by the objective lens 51, and is incident on the subject's eye E. The measurement light LS is scattered and reflected at various depth positions of the subject's eye E. The returning light of the measurement light LS from the subject's eye E advances in the same path as the forward path in the opposite direction, is guided to the fiber coupler 105, and then reaches the fiber coupler 122 via the optical fiber 128.

The fiber coupler 122 combines (interferes) the measurement light LS incident through the optical fiber 128 and the reference light LR incident through the optical fiber 121 to generate interference light. The fiber coupler 122 splits the interference light at a predetermined splitting ratio (e.g., 1:1)

to generate a pair of interference light LC. The pair of interference light LC are guided to a detector 125 through optical fibers 123 and 124, respectively.

The detector 125 is a balanced photodiode, for example. The balanced photodiode includes a pair of photodetectors that respectively detect the pair of interference light LC and output the difference between a pair of detection results acquired by the pair of photodetectors. The detector 125 sends the output (detection signal) to a DAQ (data acquisition system) 130.

The DAQ 130 is fed with a clock KC from the OCT light source 101. The clock KC is generated in the OCT light source 101 in synchronization with the output timing of each wavelength within a predetermined wavelength range performed by the wavelength tunable type light source. For example, the OCT light source 101 optically delays one of the two pieces of branched light obtained by branching the light L0 of each output wavelength, and then generates the clock KC based on the result of the detection of the combined light of the two pieces of branched light. The DAQ 130 performs sampling the detection signal input from the detector 125 based on the clock KC. The DAQ 130 sends the result of sampling the detection signal from the detector 125 to an arithmetic processor 220 of the processing unit 9. For example, the arithmetic processor 220 performs the Fourier transform, etc. on the spectral distribution based on the sampling data for each series of wavelength scanning (i.e., for each A line). With this, the reflection intensity profile for each A line is formed. In addition, the arithmetic processor 220 forms image data by applying imaging processing to the reflection intensity profiles of the respective A lines.

In the present example, the corner cube 114 is provided for changing the length of the optical path of the reference light LR (reference optical path, reference arm); however, the difference between the measurement optical path length and the reference optical path length may be changed using another kind of optical member.

The processing unit 9 calculates the refractive power value from the result of the measurement obtained by using the refractometry optical system, and controls the refractometry light source 61 and the focusing lens 74 to move respectively to positions where the fundus Ef, the refractometry light source 61, and the imaging element 59 are conjugate with each other, in the optical axis direction based on the calculated refractive power value. In some embodiments, the processing unit 9 controls the focusing lens 87 of the OCT optical system 8 to move in its optical axis direction in conjunction with the movement of the focusing lens 74. In some embodiments, the processing unit 9 controls the liquid crystal panel 41 to move in its optical axis direction in conjunction with the movement of the refractometry light source 61 and the focusing lens 74.

In the ophthalmologic apparatus 1000 according to the embodiments, the diameter (diameter in a direction orthogonal to the optical axis) of the objective lens 51 is less than the upper limit value Dmax and greater than or equal to the lower limit value Dmin, as described below. Thereby, the keratometry of projecting the measurement pattern with a size useful for corneal shape analysis onto the cornea Cr, the refractive power measurement in a wide field of view that can reduce the influence of the instrument myopia, and the OCT measurement with the scan range useful for tomographic analysis can be performed. For example, the upper limit value Dmax is prescribed so as to be capable of realizing the keratometry useful for corneal shape analysis and the refractive power measurement with high measurement accuracy by reducing the influence of the instrument myopia. For example, the lower limit value Dmin is prescribed so as to be capable of realizing the OCT measurement useful for tomographic analysis.

[Upper Limit of Diameter of Objective Lens]

Figures 3, 4:
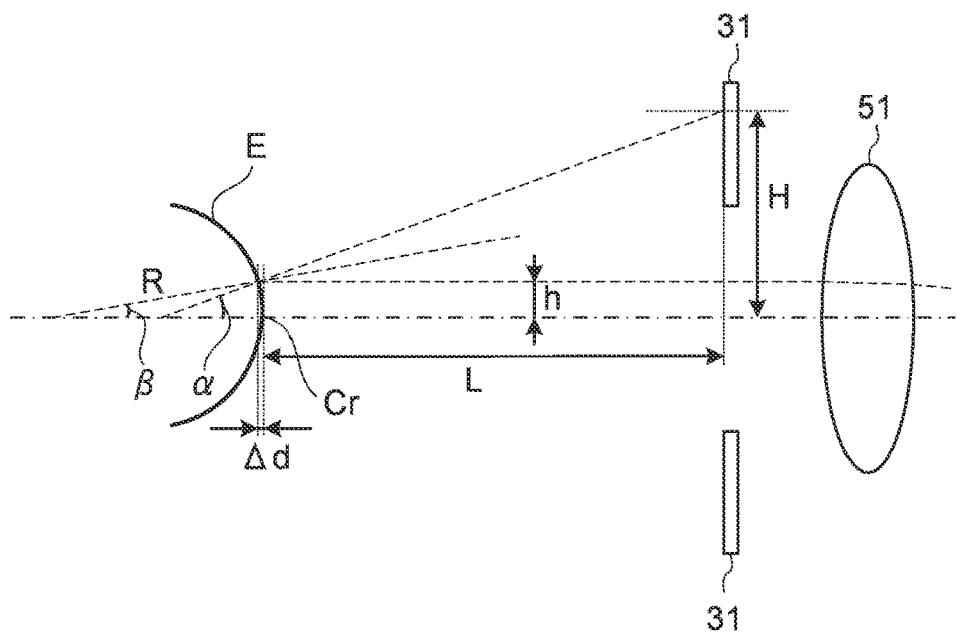
FIG. 3 is a schematic diagram for explaining an optical system of the ophthalmologic apparatus of the embodiments.
FIG. 4 is a schematic diagram for explaining an optical system of the ophthalmologic apparatus of the embodiments.

FIG. 3 shows an explanatory diagram describing the upper limit of the diameter of the objective lens 51 according to the embodiments. FIG. 3 is an enlarged view of a part of the optical system of FIG. 1. In FIG. 3, like reference numerals designate like parts as in FIG. 1, and the redundant explanation may be omitted as appropriate.

The keratometry system 3 is a telecentric optical system so that a kerato-ring image with no change in height can be acquired when the working distance changes. When light is projected onto the cornea Cr by the keratometry system 3, the cornea acts as a convex mirror and an image reflected mainly on the front surface of the cornea Cr appears.

It is assumed that the curvature radius of the cornea Cr of the subject's eye E is R, the height of the kerato-ring image with respect to the optical axis of the objective lens 51 is h, and the projection angle of the ring-shaped light flux with respect to the optical axis is a. Since the ring pattern (measurement pattern) is arranged at the incident position of the ring-shaped light flux from the kerato-ring light source 32, the following expression is satisfied. Here, an angle formed by a line, which connects the center of curvature of the cornea Cr and the incident position, and the optical axis is β.

$$h = R \times \sin(\beta) \tag{1}$$

$$\beta = \alpha/2 \tag{2}$$

It is assumed that the radius (average radius) of the kerato pattern formed on the kerato plate 31 is H0 and a distance from the kerato plate 31 to the corneal apex is L. Considering a distance $\Delta d$ ($= R - \sqrt{(R^2 - h^2)}$) between the incident position of the ring-shaped light flux and the cornea apex, the following expression is satisfied.

$$H0 = (L + (R - \sqrt{(R^2 - h^2)})) \times \tan(\alpha) + h \tag{3}$$

Furthermore, it is assumed that a radial width of the kerato pattern is $\Delta t$. The inner diameter of the kerato pattern is given by the expression (4) obtained by transforming the expression (3). It should be noted $\alpha = 2 \times \sin^{-1}(h/R)$ in the expression (4).

$$H = H0 - \Delta t/2 = (L + (R - \sqrt{(R^2 - h^2)})) \times \tan(\alpha) + h - \Delta t/2 \tag{4}$$

In order to reduce the influence of the instrument myopia as described above, it is desirable that the diameter of the objective lens 51 is as large as possible. From the above, it is desirable that the upper limit value Dmax of the diameter of the objective lens 51 is as large as possible within a range less than 2×H (inner diameter of the kerato pattern).

FIG. 4 shows a specific example of the upper limit of the diameter of the objective lens 51 according to the embodiments.

For example, h=1.5 millimeters in order to measure the corneal shape of the area of φ3 on the cornea Cr useful for corneal shape analysis. Assuming that the curvature radius of the subject's eye E is 8 millimeters and L=49.5 millimeters, the projection angle α is approximately 21.6 degrees and the diameter (average diameter) of the kerato pattern is 2×H=42.22455 millimeters.

Assuming that the radial width of the kerato pattern $\Delta t$ is 0.05 millimeters, the inner diameter of the kerato pattern is 41.44778 millimeters and the outer diameter of the kerato pattern is 43.00543 millimeters.

Therefore, it is desirable that the upper limit value Dmax of the diameter of the objective lens 51 is as large as possible within a range less than 41.44778 millimeters.

[Lower Limit of Diameter of Objective Lens]

Figure 5:
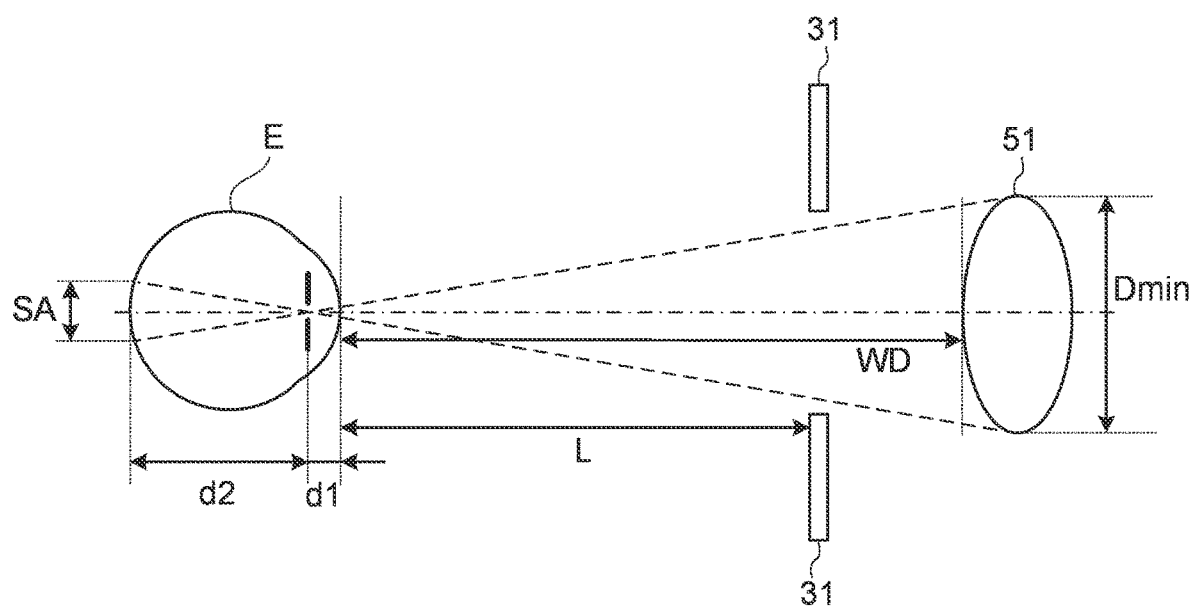
FIG. 5 is a schematic diagram for explaining an optical system of the ophthalmologic apparatus of the embodiments.

FIG. 5 shows an explanatory diagram describing the lower limit of the diameter of the objective lens 51 according to the embodiments. FIG. 5 is an enlarged view of a part of the optical system of FIG. 1. In FIG. 5, like reference numerals designate like parts as in FIG. 1, and the redundant explanation may be omitted as appropriate.

In order to exhaustively acquire data of a desired scan range, the optical scanner 88 deflects the measurement light LS in each of the X direction and the Y direction. Assuming that the scan range of the fundus Ef is a range of diameter RA, it is necessary for the optical scanner 88 to deflect by at least $RA \times \sqrt{2}$ (=SA) in each direction.

Here, the optical scanner 88 is disposed at a position optically conjugate with the pupil of the subject's eye E. It is assumed that the working distance is WD, a distance from the corneal apex to the pupil is d1, and a distance from the pupil to the fundus is d2. The lower limit value Dmin of the diameter of the objective lens 51 satisfies the following expression from the homothetic relationship between a triangle whose apex is the pupil and whose base is the radius of the objective lens 51 and a triangle whose apex is the pupil and whose base is the scan range SA/2 on the fundus.

$$Dmin = (WD + d1) \times SA/d2 \quad (5)$$

As described above, in order to perform OCT measurement with SA square range as the scan range, the diameter of the objective lens 51 needs to be greater than or equal to Dmin.

For example, the size of the macular region on the fundus Ef is in the range of 2 millimeters in diameter. Therefore, assuming that the scan range is $2 \times \sqrt{2}$ square, the working distance is 63 millimeters, d1 is 3 millimeters, and d2 is 21 (=24-3) millimeters, the lower limit value Dmin is approximately 8.9 millimeters.

Figure 6:
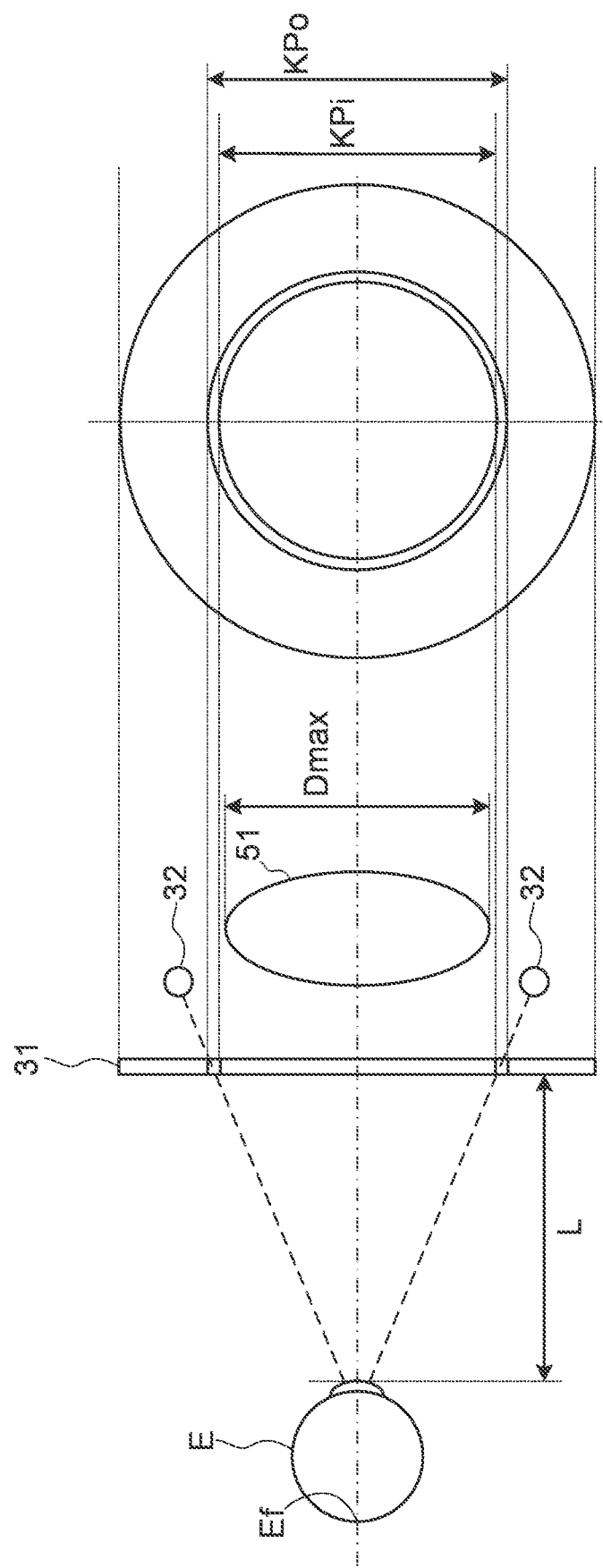
FIG. 6 is a schematic diagram for explaining an optical system of the ophthalmologic apparatus of the embodiments.

FIG. 6 schematically shows a relationship between the objective lens 51 and the kerato plate 31. Like reference numerals designate like parts in FIGS. 1 and 6.

In FIG. 6, the kerato pattern whose inner diameter is Kpi and whose outer diameter is Kpo is formed in the kerato plate 31. As shown in FIG. 4, it is desirable that the diameter of the objective lens 51 is in a range less than the inner diameter Kpi of the kerato pattern formed in the kerato plate 31. The inner diameter Kpi is obtained by 2×H. Therefore, it is desirable that the diameter of the objective lens 51 is in a range less than 2×H.

Further, as shown in FIG. 5, it is desirable that the diameter of the objective lens 51 is a size that allows the OCT measurement with a desired scan range on the fundus Ef. For example, it is desirable that the diameter of the objective lens 51 is greater than or equal to the lower limit value Dmin so as to be capable of perform OCT measuring on at least the macular region.

<Configuration of Processing System>

Figure 7:
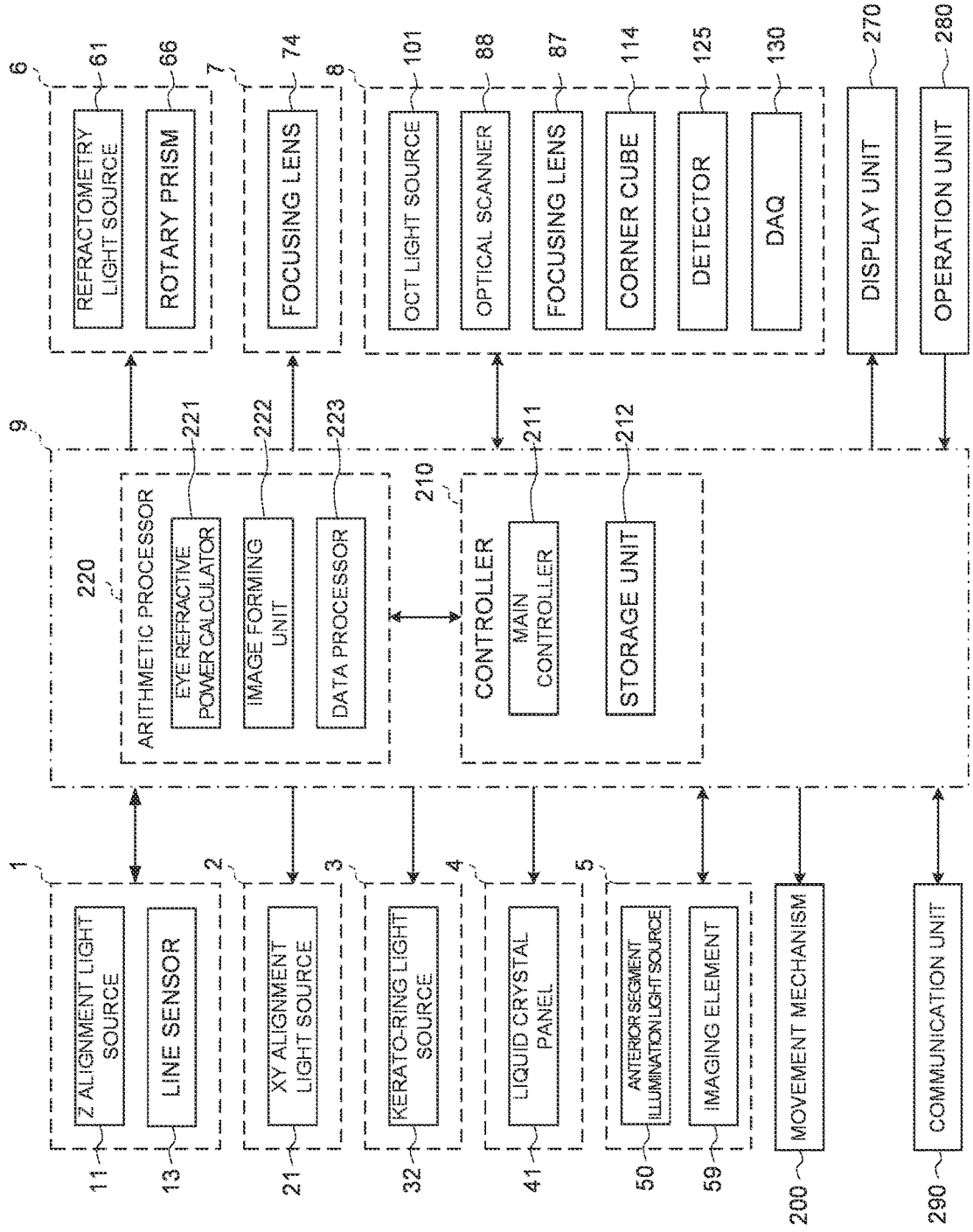
FIG. 7 is a schematic diagram illustrating an example of a configuration of a processing system of the ophthalmologic apparatus according to the embodiments.

The processing system of the ophthalmologic apparatus 1000 will be described. FIG. 7 illustrates an example of the functional structure of the processing system of the ophthalmologic apparatus 1000. FIG. 7 shows an example of a functional block diagram illustrating the processing system of the ophthalmologic apparatus 1000.

The processing unit 9 controls each part of the ophthalmologic apparatus 1000. Further, the processing unit 9 is capable of performing various types of arithmetic processing. The processing unit 9 includes a processor. The function of the processor is implemented by a circuit(s) such as, for example, a CPU (central processing unit), a GPU (graphics processing unit), an ASIC (application specific integrated circuit), and a PLD (programmable logic device). Examples of PLD include a simple programmable logic device (SPLD), a complex programmable logic device (CPLD), and a field programmable gate array (FPGA). The processing unit 9 realizes the function according to the embodiments, for example, by read out a computer program stored in a storage circuit or a storage device and executing the computer program.

The processing unit 9 includes a controller 210 and the arithmetic processor 220. Further, the ophthalmologic apparatus 1000 includes a movement mechanism 200, a display unit 270, an operation unit 280, and a communication unit 290.

The movement mechanism 200 is a mechanism for moving a head unit in front, back, left and right directions, the head unit housing the optical systems such as the Z alignment system 1, the XY alignment system 2, the keratometry system 3, the fixation projection system 4, the anterior segment observation system 5, the refractometry projection system 6, the refractometry light reception system 7, the OCT optical system 8, and the like. For example, the movement mechanism 200 is provided with an actuator that generates driving force for moving the head unit and a transmission mechanism that transmits the driving force to the head unit. The actuator is configured by a pulse motor, for example. The transmission mechanism is configured by a combination of gears, a rack and pinion, and the like, for example. The controller 210 (main controller 211) controls the movement mechanism 200 by sending a control signal to the actuator.

(Controller 210)

The controller 210 includes a processor and controls each part of the ophthalmologic apparatus. The controller 210 includes the main controller 211 and a storage unit 212. The storage unit 212 stores, in advance, a computer program for controlling the ophthalmologic apparatus. The computer program includes light source control programs, detector control programs, optical scanner control programs, optical system control programs, arithmetic processing programs, programs for user interface, and the like. The main controller 211 operates according to the computer programs, and thereby the controller 210 performs the control processing.

The main controller 211 performs various controls of the ophthalmologic apparatus, as a measurement controller. Examples of control of the Z alignment system 1 include control of the Z alignment light source 11, control of the line sensor 13, and the like. Examples of the control of the Z alignment light source 11 include turning on and off of the light source, adjustment of amount of light, adjustment of aperture, and the like. Examples of the control of the line sensor 13 include adjustment of exposure of a detecting element, adjustment of gain of a detecting element, adjustment of detecting rate of a detecting element, and the like. Thereby, the Z alignment light source 11 can be switched between lighting and non-lighting or light amount can be changed. The main controller 211 acquires a signal detected by the line sensor 13 and specifies the projection position of light onto the line sensor 13 based on the acquired signal. The main controller 211 obtains a position of the corneal apex of the subject's eye E based on the specified projection position and the position of the bright spot image obtained by the XY alignment system 2, and controls the movement mechanism 200 based on the obtained position of the corneal apex of the subject's eye E to move the head unit in front and back directions (Z alignment).

Examples of control of the XY alignment system 2 include control of the XY alignment light source 21, and the like. Examples of the control of the XY alignment light source 21 include turning on and off of the light source, adjustment of amount of light, adjustment of aperture, and the like. Thereby, the XY alignment light source 21 can be switched between lighting and non-lighting, or light amount can be changed. The main controller 211 acquires a signal detected by the imaging element 59, and specifies a position of a bright spot image on the basis of returning light of the light from the XY alignment light source 21 based on the acquired signal. The main controller 211 controls the movement mechanism 200 to move the head unit in left, right, up, down directions so as to cancel a displacement the position of the bright spot image with respect to a predetermined target position (for example, a center position of the alignment mark AL) (XY alignment).

Examples of control for the keratometry system 3 include control of the kerato-ring light source 32, and the like. Examples of the control of the kerato-ring light source 32 include turning on and off of the light source, adjustment of light amount, adjustment of aperture, and the like. Thereby, the kerato-ring light source 32 can be switched between lighting and non-lighting, or light amount can be changed. The main controller 211 controls the arithmetic processor 220 to perform a known calculation on a kerato-ring image detected by the imaging element 59. Thereby, corneal shape parameters of the subject's eye E are obtained.

Examples of control for the fixation projection system 4 include control of the liquid crystal panel 41 and the like. Examples of the control of the liquid crystal panel 41 include displaying on and off of the fixation target, switching the display position of the fixation target, and the like. Thereby, the fixation target is projected onto the fundus Ef of the subject's eye E. For example, the fixation projection system 4 includes a movement mechanism that moves the liquid crystal panel 41 (or the liquid crystal panel 41 and the relay lens 42) in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move at least the liquid crystal panel 41 in the optical axis direction. Thereby, the position of liquid crystal panel 41 is adjusted so that the liquid crystal panel 41 and the fundus Ef are optically conjugate with each other.

Examples of the control for the anterior segment observation system 5 include control of an anterior segment illumination light source 50, control of the imaging element 59, and the like. Examples of control of the anterior segment illumination light source 50 include turning on and off the light source, adjustment of light amount, adjustment of aperture, and the like. Thereby, the anterior segment illumination light source 50 can be switched between lighting and non-lighting, or light amount can be changed. Example of the control of the imaging element 59 include adjustment of exposure of the imaging element 59, adjustment of gain of the imaging element 59, adjustment of detecting rate of the imaging element 59, and the like. The main controller 211 acquires a signal detected by the imaging element 59 and controls the arithmetic processor 220 to perform processing such as forming image based on the acquired signal and the like.

Examples of control for the refractometry projection system 6 include control of the refractometry light source 61, control of the rotary prism 66, and the like. Examples of the control of the refractometry light source 61 include turning on and off of the light source, adjustment of light amount, and the like. Thereby, the refractometry light source 61 can be switched between lighting and non-lighting, or light amount can be changed. For example, the refractometry projection system 6 includes a movement mechanism that moves the refractometry light source 61 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the refractometry light source 61 in the optical axis direction. Examples of the control of the rotary prism 66 include control of rotating the rotary prism 66 and the like. For example, a rotary mechanism that rotates the rotary prism 66 is provided and the main controller 211 controls the rotary mechanism to rotate the rotary prism 66.

Examples of control for refractometry light reception system 7 include control of the focusing lens 74, and the like. Examples of the control of the focusing lens 74 include control of moving the focusing lens 74 in the optical axis direction. For example, the refractometry light reception system 7 include a movement mechanism that moves the focusing lens 74 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the focusing lens 74 in the optical axis direction. The main controller 211 is capable of moving the refractometry light source 61 and the focusing lens 74 in the optical axis direction respectively depending on the refractive power of the subject's eye E for example so that the refractometry light source 61 and the fundus Ef and the imaging element 59 are optically conjugate with each other.

Examples of control for the OCT optical system 8 include control of the OCT light source 101, control of the optical scanner 88, control of the focusing lens 87, control of the corner cube 114, control of the detector 125, control of the DAQ 130, and the like. Examples of the control of the OCT light source 101 includes turning on and off of the light source, adjustment of light amount, adjustment of aperture, and the like. Examples of the control of the optical scanner 88 include control of the scanning position and the scan range and the scanning speed by means of the first galvano mirror, control of the scanning position and the scan range and the scanning speed by means of the second galvano mirror, and the like.

Examples of the control of the focusing lens 87 include control of moving the focusing lens 87 in the optical axis direction, control of moving the focusing lens 87 to the in-focus reference position corresponding to the photographing site, control of moving the focusing lens 87 within the movement range (in-focus range) corresponding to the photographing site, and the like. For example, the OCT optical system 8 include a movement mechanism that moves the focusing lens 87 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the focusing lens 87 in the optical axis direction. In some embodiments, the ophthalmologic apparatus is provided with a holding member that holds the focusing lens 74 and the focusing lens 87, and the driver that drives the holding member. The main controller 211 controls the driver to move the focusing lenses 74 and 87. For example, the main controller 211 may moves the focusing lens 87 alone based on the intensity of the interference signal, after moving the focusing lens 87 in conjunction with the movement of the focusing lens 74.

Examples of the control of the corner cube 114 include control of moving the corner cube 114 along the optical path of the corner cube 114. For example, the OCT optical system 8 include a movement mechanism that moves the corner cube 114 along the optical path. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the corner cube 114 along the optical path. Examples of the control of the detector 125 include adjustment of exposure of a detecting element, adjustment of gain of a detecting element, adjustment of detecting rate of a detecting element, and the like. The main controller 211 controls the DAQ 130 to perform sampling of the signal detected by the detector 125 and controls the arithmetic processor 220 (image forming unit 222) to perform processing such as forming image based on the sampled signal and the like.

Further, the main controller 211 performs a process of writing data in the storage unit 212 and a process of retrieving data from the storage unit 212.

(Storage Unit 212)

The storage unit 212 stores various types of data. Examples of the data stored in the storage unit 212 include a measurement result of the objective measurement, image data of a tomographic image, image data of a fundus image, subject's eye information, and the like. The subject's eye information includes information on the subject such as patient ID and name, and information on the subject's eye such as identification information of the left eye/right eye. The storage unit 212 further stores various types of programs and data to run the ophthalmologic apparatus.

(Arithmetic Processor 220)

The arithmetic processor 220 includes an eye refractive power calculator 221, the image forming unit 222, and a data processor 223.

The eye refractive power calculator 221 analyzes a ring image (pattern image) acquired by receiving the returning light of the ring-shaped light flux (ring-shaped measurement pattern) projected onto the fundus Ef by the refractometry projection system 6 by the imaging element 59. For example, the eye refractive power calculator 221 obtains a position of the center of gravity of the ring image from the brightness distribution in the image representing the acquired ring image, obtains brightness distributions along a plurality of scanning directions extending radially from the position of the center of gravity, and specifies a ring image from this brightness distributions. Subsequently, the eye refractive power calculator 221 obtains an approximate ellipse of the specified ring image and obtains a spherical power, an astigmatic power, and an astigmatic axis angle by assigning a major axis and a minor axis of the approximate ellipse to a known formula. Alternatively, the eye refractive power calculator 221 can obtain the eye refractive power parameter based on deformation and displacement of the ring image with respect to the reference pattern.

Further, the eye refractive power calculator 221 calculates a corneal refractive power, a corneal astigmatism power, and a corneal astigmatic axis angle based on the kerato-ring image acquired by the anterior segment observation system 5. For example, the eye refractive power calculator 221 calculates a corneal curvature radius of the steepest meridian and/or the flattest meridian of the anterior surface of the cornea by analyzing the kerato-ring image and calculates above parameters based on the corneal curvature radius.

The image forming unit 222 forms image data of a tomographic image of the fundus Ef based on a signal detected by the detector 115. That is, the image forming unit 222 forms the image data of the subject's eye E based on a detection result of the interference light LC obtained by the interference optical system. Like the conventional spectral-domain-type OCT, this process includes processes such as filtering and FFT (Fast Fourier Transform). The image data acquired in this manner is a data set including a group of image data formed by imaging the reflection intensity profiles of a plurality of A lines. Here, the A lines are the paths of the measurement light LS in the subject's eye E.

In order to improve the image quality, it is possible to repeatedly perform scan with the same pattern a plurality of times to collect a plurality of data sets, and to compose (i.e., average) the plurality of data sets.

The data processor 223 performs various kinds of data processing (e.g., image processing) and various kinds of analysis on a tomographic image formed by the image forming unit 222. For example, the data processor 223 performs various correction processes such as brightness correction and dispersion correction of images. Further, the data processor 223 performs various types of image processing and analysis on images (anterior segment image, etc.) acquired using the anterior segment observation system 5.

The data processor 223 can form volume data (voxel data) of the subject's eye E by performing known image processing such as interpolation processing for interpolating pixels between tomographic images. In the case of displaying an image based on the volume data, the data processor 223 performs a rendering processing on the volume data so as to form a pseudo three-dimensional image viewed from a specific line-of-sight direction.

(Display Unit 270, Operation Unit 280)

Upon receiving control of the controller 210, the display unit 270 displays information, as a user interface unit. The display unit 270 includes the display unit 10 as illustrated in FIG. 1 and the like.

The operation unit 280 is used to operate the ophthalmologic apparatus, as the user interface unit. The operation unit 280 includes various types of hardware keys (the joystick, buttons, switches, etc.) provided in the ophthalmologic apparatus. Further, the operation unit 280 may include various kinds of software keys (buttons, icons, menus, etc.) displayed on the touch panel type display screen 10a.

At least part of the display unit 270 and the operation unit 280 may be integrally configured. A typical example of this is the touch-panel display screen 10a.

(Communication Unit 290)

The communication unit 290 has the function of communicating with an external device (not shown). The communication unit 290 includes a communication interface according to the mode of communication with an external device. Examples of the external device includes an eyeglass lens measurement device for measuring the optical properties of lenses. The eyeglass lens measurement device measures the power of the eyeglass lens worn by the subject and inputs the measurement data to the ophthalmologic apparatus 1000. The external device may also be a device (reader) having the function of reading information from a recording medium or a device (writer) having the function of writing information to a recording medium. Further, the external device may be a hospital information system (HIS) server, a Digital Imaging and Communications in Medicine (DI-COM) server, a doctor terminal, a mobile terminal, a personal terminal, a cloud server, or the like. The communication unit 290 may be provided in the processing unit 9, for example.

The refractometry projection system 6 and the refractometry light reception system 7 are an example of the "refractive power measurement optical system" according to the embodiments. The OCT optical system 8 is an example of the "inspection optical system" according to the embodiments. The keratometry system 3 is an example of the "corneal shape measurement optical system" according to the embodiments. The kerato-ring light source 32 is an example of the "keratometry light source" according to the embodiments.

OPERATION EXAMPLE

The operation of the ophthalmologic apparatus 1000 according to the embodiments will be described.

FIG. 8 illustrates an example of the operation of the ophthalmologic apparatus 1000. FIG. 8 shows a flowchart of an example of the operation of the ophthalmologic apparatus 1000. The storage unit 212 stores a of computer programs for realizing the processing shown in FIG. 8. The main controller 211 operates according to the computer programs, and thereby the main controller 211 performs the processing shown in FIG. 8.

(S1: Perform Alignment)

When the examiner performs a predetermined operation on the operation unit 280 in a state where the face of the subject is fixed to a face supporter (not shown), the ophthalmologic apparatus 1000 performs alignment.

Specifically, the main controller 211 turns on the Z alignment light source 11 and the XY alignment light source 21. Furthermore, the main controller 211 turn on the anterior segment illumination light source 50. The processing unit 9 acquires imaging signal of an anterior segment image formed on the imaging surface of the imaging element 59 and controls the display unit 270 to display the anterior segment image. After that, the optical system shown in FIG. 1 is moved to at the inspection position of the subject's eye E. The inspection position is a position where the inspection of the subject's eye E can be performed with sufficient accuracy. The subject's eye E is placed at the inspection position through the alignment described above (that is, by the use of the Z alignment system 1, the XY alignment system 2, and the anterior segment observation system 5). The movement of the optical system is performed by the controller 210 according to operation or instruction from a user, or instruction by the controller 210. That is, the movement of the optical system to the inspection position of the subject's eye E and the preparation for the objective measurement are carried out. This alignment is performed as needed until the measurement is completed.

Further, the main controller 211 moves the refractometry light source 61, the focusing lens 74, and the liquid crystal panel 41 along the respective optical axes to the origin positions (for example, the position corresponding to 0 D).

(S2: Perform Keratometry)

Next, the main controller 211 controls the liquid crystal panel 41 to display the pattern representing the fixation target at a display position corresponding to the desired fixation position. Thereby, the subject's eye E is gazed at the desired fixation position.

After that, the main controller 211 turns on the kerato-ring light source 32. When the light is emitted from the kerato-ring light source 32, a ring-shaped light beam for corneal shape measurement is projected onto the cornea Cr of the subject's eye E. The eye refractive power calculator 221 applies arithmetic processing to the image acquired by the imaging element 59 to calculate the corneal curvature radius. Furthermore, based on the calculated corneal curvature radius, the eye refractive power calculator 221 calculates the corneal refractive power, the corneal astigmatic power, and the corneal astigmatic axis angle. The calculated corneal refractive power and the like are stored in the storage unit 212 in the controller 210. Upon reception of an instruction from the main controller 211, an operation or instruction on the operation unit 280 by the user, the operation of the ophthalmologic apparatus 1000 proceeds to step S3. It should be noted that the keratometry may be performed at the same time when acquiring the ring image in the next refractometry or may be performed continuously when acquiring the ring image in the next refractometry.

(S3: Perform Refractive Power Measurement)

Next, the main controller 211 controls the liquid crystal panel 41 to project the fixation target onto the subject's eye E and performs the refractive power measurement.

In the refractometry, the main controller 211 causes a ring-shaped measurement pattern light flux for refractometry to be projected onto the subject's eye E as described above. The ring image based on the returning light of the measurement pattern light flux from the subject's eye E is imaged on the imaging surface of the imaging element 59. The main controller 211 determines whether or not the ring image based on the returning light from the fundus Ef detected by the imaging element 59 can be acquired. For example, the main controller 211 detects a position (pixel) of the edge of the image that is formed based on the returning light detected by the imaging element 59, and determines whether or not the width (difference between outer diameter and inner diameter) of the image is greater than or equal to a predetermined value. Alternatively, the main controller 211 may determine whether or not the ring image can be acquired by determining whether or not a ring can be formed based on points (image) having a predetermined height (ring diameter) or more.

When it is determined that the ring image can be acquired, the eye refractive power calculator 221 analyzes the ring image based on the returning light of the measurement pattern light flux projected onto the subject's eye E by a known method, and calculates a provisional spherical power S and a provisional astigmatic power C. Based on the obtained provisional spherical power S and the obtained provisional astigmatic power C, the main controller 211 sets the refractometry light source 61, the focusing lens 74, and the liquid crystal panel 41 to respective positions of the equivalent spherical power (S+C/2) (positions corresponding to a provisional far point). After that, the ring image is acquired once again, the acquired ring image is analyzed, and a provisional spherical power S and a provisional astigmatic power C is obtained. And the refractometry light source 61 and the like is moved from the position moved by the first measurement for fine adjustment. The main controller 211 moves the liquid crystal panel 41 further to the fogging position from the position, and then controls the refractometry projection system 6 and the refractometry light reception system 7 to acquire a ring image again as the main measurement. The main controller 211 controls the eye refractive power calculator 221 to calculate a spherical power, an astigmatic power, and an astigmatic axis angle from the result obtained by analyzing the ring image acquired in the same manner as described above and the movement amount of the focusing lens 74.

Further, the eye refractive power calculator 221 obtains a position corresponding the far point of the subject's eye E (position corresponding to the far point obtained by the main measurement) from the obtained spherical power and the obtained astigmatic power. The main controller 211 moves the liquid crystal panel 41 to the position corresponding to the obtained far point. In the controller 210, the position of the focusing lens 74, the calculated spherical power, and the like are stored in the storage unit 212. Upon reception of an instruction from the main controller 211, an operation or instruction on the operation unit 280 by the user, the operation of the ophthalmologic apparatus 1000 proceeds to step S4.

When it is determined that the ring image can not be acquired, the main controller 211 moves the refractometry light source 61 and the focusing lens 74 to the minus power side (for example, −10 D) or the plus power side (for example, +10 D) in a preset step, considering the possibility of high refractive error of the eye. The main controller 211 controls the refractometry light reception system 7 to detect the ring image at each position. If it is still determined that the ring image can not be acquired, the main controller 211 executes a predetermined measurement error process. In this case, the operation of the ophthalmologic apparatus 1000 may proceed to step S4. In the controller 210, information indicating that the result of refractometry can not be acquired is stored in the storage unit 212.

The focusing lens 87 of the OCT optical system 8 is moved in the optical axis direction in conjunction with the movement of the refractometry light source 61 and the focusing lens 74.

(S4: Acquire Tomographic Image)

Next, the main controller 211 controls the liquid crystal panel 41 to project the fixation target onto the subject's eye E and performs the OCT measurement.

The main controller 211 turns on the OCT light source 101 and controls the optical scanner 88 so as to scan a predetermined site of the fundus Ef with the measurement light LS. A detection signal obtained by scanning with the measurement light LS is fed to the image forming unit 222. The image forming unit 222 forms a tomographic image of the fundus Ef based on the obtained detection signal. Thus, the operation of the ophthalmologic apparatus 1000 is terminated (END).

From the above, in case that the objective lens 51 is shared by the refractometry optical system and the OCT optical system 8, the diameter of the objective lens 51 can be designed as large as possible within a range less than the inner diameter of the kerato pattern. Thereby, the ophthalmologic apparatus that is capable of obtaining a useful keratometry analysis result and of performing the refractive power measurement in a wide field of view to reduce the influence of the instrument myopia without changing the working distance, while performing kerato illumination from the outer edge side of the objective lens 51, can be provided.

Furthermore, the diameter of the objective lens 51 is greater than or equal to the lower limit value so as to secure the scan range for performing OCT measurement on the macular region. Thereby, the ophthalmologic apparatus that is capable of obtaining useful tomographic analysis result (analysis result of tomographic image, layer thickness distribution, layer thickness information etc.) without changing the working distance can be provided.

In the aforementioned embodiment, the case has been described in which the inspection optical system including the optical scanner is the OCT optical system. However, the configuration of the ophthalmologic apparatus according to the embodiments is not limited thereto. The inspection optical system according to some embodiments includes the SLO optical system. The SLO optical system is an optical system for scanning the fundus Ef with light using the optical scanner and detecting returning light of the light using a light-receiving device. In some embodiments, the SLO optical system acquires a front image of the fundus Ef by laser scanning using a confocal optical system. The SLO optical system includes the optical scanner, an SLO projection system that deflects light from an SLO light source using the optical scanner and projects the deflected light onto the subject's eye E, and an SLO light receiving system that receives returning light of the light.

Even in this case, the diameter of the objective lens 51 is designed to be greater than or equal to the lower limit value so as to secure at least the scan range where the front image of the macular region can be acquired. Thereby, the ophthalmologic apparatus that is capable of acquiring useful analysis result of the front image without changing the working distance can be provided.

[Actions and Effects]

Described below are the actions and effects of the ophthalmologic apparatus according to the embodiments.

The ophthalmologic apparatus (1000) according to some embodiments includes an objective lens (51), a refractive power measurement optical system (refractometry projection system 6, refractometry light reception system 7), an inspection optical system (OCT optical system 8), and a corneal shape measurement optical system (keratometry system 3). The refractive power measurement optical system is configured to project light onto a subject's eye (E) via the objective lens and to detect returning light from the subject's eye. The inspection optical system includes an optical scanner (88) and is configured to deflect light from a light source, to project the light deflected by the optical scanner onto the subject's eye via the objective lens, and to detect returning light from the subject's eye. The corneal shape measurement optical system is configured to project an arc-like or circumferential measurement pattern from an outer edge side of the objective lens onto the subject's eye and to detect returning light from a cornea (Cr) of the subject's eye. When a working distance is WD, a distance from a corneal apex of the subject's eye to a pupil of the subject's eye is d1, a distance from the pupil to a fundus (Ef) of the subject's eye is d2, and a scan range by the optical scanner is SA square, a diameter of the objective lens is greater than or equal to $((WD+d1)\times SA/d2)$.

According to such a configuration, in case that the objective lens is shared by the refractive power measurement optical system and the inspection optical system, with illumination from the outer edge side of the objective lens, the inspection in the scan range of SA square (SA×SA) on the fundus can be performed without changing the working distance. Thereby, the diameter of the objective lens can be optimized without deteriorating the measurement range and the measurement accuracy by a plurality of optical systems corresponding to the type of the objective measurement can be provided. As a result, the ophthalmologic apparatus can be downsized. Further, useful inspection results can be acquired by scanning with a desired scan range on the fundus.

In the ophthalmologic apparatus according to some embodiments, the scan range is a range of $(2 \times \sqrt{2})$ millimeters square or larger on the fundus of the subject's eye.

According to such a configuration, the ophthalmologic apparatus that is capable of acquiring useful inspection results by scanning the macular region on the fundus without changing the working distance.

In the ophthalmologic apparatus according to some embodiments, the corneal shape measurement optical system includes a keratometry light source (kerato-ring light source 32) and a keratometry plate (kerato plate 31) that is disposed between the keratometry light source and the subject's eye and is formed a light transmitting part (kerato pattern) which penetrates light from the keratometry light source. The corneal shape measurement optical system is configured to project the measurement pattern onto the cornea of the subject's eye around an optical axis of the objective lens. When a distance between the corneal apex of the subject's eye and the keratometry plate is L, a height of an image based on the measurement pattern with respect to the optical axis of the objective lens is h, a corneal curvature radius of the subject's eye is R, and a radial width of the measurement pattern is $\Delta t$, the diameter of the objective lens is less than $2 \times ((L+(R-\sqrt{(R^2-h^2)})) \times \tan(2 \times \sin^{-1}(h/R))+h-\Delta t/2)$.

According to such a configuration, the diameter of the objective lens can be designed as large as possible in a range less than the inner diameter of the light transmitting part formed in the keratometry plate. Thereby, the ophthalmologic apparatus that is capable of obtaining useful keratometry analysis results and of performing the refractive power measurement in a wide field of view to reduce the influence of the instrument myopia without changing the working distance can be provided.

The ophthalmologic apparatus (1000) according to some embodiments includes an objective lens (51), a refractive power measurement optical system (refractometry projection system 6, refractometry light reception system 7), an inspection optical system (OCT optical system 8), and a corneal shape measurement optical system (keratometry system 3). The refractive power measurement optical system is configured to project light onto a subject's eye (E) via the objective lens and to detect returning light from the subject's eye. The inspection optical system includes an optical scanner (88) and is configured to deflect light from a light source, to project the light deflected by the optical scanner onto the subject's eye via the objective lens, and to detect returning light from the subject's eye. The corneal shape measurement optical system is configured to project an arc-like or circumferential measurement pattern from an outer edge side of the objective lens onto the subject's eye and to detect returning light from a cornea (Cr) of the subject's eye. The corneal shape measurement optical system includes a keratometry light source (kerato-ring light source 32), a keratometry plate (karato plate 31) that is disposed between the keratometry light source and the subject's eye and is formed a light transmitting part (kerato pattern) which penetrates light from the keratometry light source. The corneal shape measurement optical system is configured to project the measurement pattern onto the cornea of the subject's eye around an optical axis of the objective lens. When a distance between the corneal apex of the subject's eye and the keratometry plate is L, a height of an image based on the measurement pattern with respect to the optical axis of the objective lens is h, a corneal curvature radius of the subject's eye is R, and a radial width of the measurement pattern is $\Delta t$, the diameter of the objective lens is less than $2 \times ((L+(R-\sqrt{(R^2-h^2)})) \times \tan(2 \times \sin^{-1}(h/R))+h-\Delta t/2)$.

Thereby, the ophthalmologic apparatus that is capable of obtaining a useful keratometry analysis result and of performing the refractive power measurement in a wide field of view to reduce the influence of the instrument myopia without changing the working distance, while illuminating from the outer edge side of the objective lens, can be provided. Thereby, the diameter of the objective lens can be optimized without deteriorating the measurement range and the measurement accuracy by a plurality of optical systems corresponding to the type of the objective measurement can be provided. As a result, the ophthalmologic apparatus can be downsized.

In the ophthalmologic apparatus according to some embodiments, the height of the image based on the measurement pattern is 1.5 millimeters.

According to such a configuration, a shape measurement of 3 millimeters on the cornea can be performed. Thereby, the corneal shape measurement useful for corneal shape analysis can be performed.

In the ophthalmologic apparatus according to some embodiments, the inspection optical system includes an OCT optical system (8) configured to split light (L0) from an OCT light source (101) into reference light (LR) and measurement light (LS), to deflect the measurement light using the optical scanner, to project the deflected measurement light onto the subject's eye, and to detect interference light (LC) between returning light of the measurement light from the subject's eye and the reference light.

According to such a configuration, the ophthalmologic apparatus that is capable of acquiring useful tomographic analysis results by scanning a desired scan range on the fundus without changing the working distance.

In the ophthalmologic apparatus according to some embodiments, the inspection optical system includes an SLO optical system configured to deflect light from an SLO light source, to project the deflected light onto the subject's eye, and to receive returning light of the light.

According to such a configuration, the ophthalmologic apparatus that is capable of acquiring useful analysis results of the fundus image by scanning a desired scan range on the fundus without changing the working distance.

<Others>

The above-described embodiments are merely examples for carrying out the present invention. Those who intend to implement the present invention can apply any modification, omission, addition, or the like within the scope of the gist of the present invention.

For example, the diameter of the objective lens 51 according to the embodiments may be at least less than the upper limit value Dmax. The diameter of the objective lens 51 according to the embodiments may be at least greater than or equal to the lower limit value Dmin.

Further, in the embodiments described above, the case has been described in which the ophthalmologic apparatus performs OCT on the fundus Ef. However, the configuration of the ophthalmologic apparatus according to the embodiments is not limited thereto. For example, the present invention can be applied to an ophthalmologic apparatus that performs OCT on the fundus Ef and the anterior segment.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus comprising:
an objective lens;
a refractive power measurement optical system configured to project light onto a subject's eye via the objective lens and to detect returning light from the subject's eye;
an inspection optical system that includes an optical scanner and is configured to deflect light from a light source, to project the light deflected by the optical scanner onto the subject's eye via the objective lens, and to detect returning light from the subject's eye; and
a corneal shape measurement optical system configured to project an arc-like or circumferential measurement pattern from an outer edge side of the objective lens onto the subject's eye and to detect returning light from a cornea of the subject's eye, wherein
when a working distance is WD, a distance from a corneal apex of the subject's eye to a pupil of the subject's eye is d1 a distance from the pupil to a fundus of the subject's eye is d2, and a scan range by the optical scanner is SA square, a diameter of the objective lens is greater than or equal to $((WD+d1) \times SA/d2)$, wherein the corneal shape measurement optical system comprises:
a keratometry light source; and
a keratometry plate that is disposed between the keratometry light source and the subject's eye and is formed a light transmitting part which penetrates light from the keratometry light source, wherein
the corneal shape measurement optical system is configured to project the measurement pattern onto the cornea of the subject's eye around an optical axis of the objective lens, and
when a distance between the corneal apex of the subject's eye and the keratometry plate is L, a height of an image based on the measurement pattern with respect to the optical axis of the objective lens is h, a corneal curvature radius of the subject's eye is R, and a radial width of the measurement pattern is $\Delta t$, the diameter of the objective lens is less than $2 \times ((L+(R-\sqrt{(R^2-h^2)})) \times \tan(2 \times \sin^{-1}(h/R)) + h - \Delta t/2)$.

2. The ophthalmologic apparatus of claim 1, wherein the scan range is a range of $(2 \times \sqrt{2})$ millimeters square or larger on the fundus of the subject's eye.

3. The ophthalmologic apparatus of claim 1, wherein the height of the image based on the measurement pattern is 1.5 millimeters.

4. The ophthalmologic apparatus of claim 1, wherein the inspection optical system includes an OCT optical system configured to split light from an OCT light source into reference light and measurement light, to deflect the measurement light using the optical scanner, to project the deflected measurement light onto the subject's eye, and to detect interference light between returning light of the measurement light from the subject's eye and the reference light.

5. The ophthalmologic apparatus of claim 1, wherein the inspection optical system includes an SLO optical system configured to deflect light from an SLO light source, to project the deflected light onto the subject's eye, and to receive returning light of the light.

* * * * *